United States Patent [19]

Lemchen et al.

[11] 4,141,956
[45] Feb. 27, 1979

[54] COLD STERILIZER

[76] Inventors: Marc S. Lemchen, 219 E. 81st St., New York, N.Y. 10028; Ian M. Chong, 17 Monroe Pl. #1A, Brooklyn Heights, N.Y. 11201; Carlton Klein, 69-05C 186 La., Fresh Meadows, N.Y. 11365

[21] Appl. No.: 876,961

[22] Filed: Feb. 13, 1978

[51] Int. Cl.² .............................................. A61L 3/00
[52] U.S. Cl. .................................... 422/116; 422/117; 422/119; 422/301
[58] Field of Search ...................... 21/99, 100, 87, 90, 21/91, 103

[56] References Cited

U.S. PATENT DOCUMENTS

| | | | |
|---|---|---|---|
| 1,762,448 | 6/1930 | MacDuffee et al. | 21/99 X |
| 2,327,721 | 8/1943 | Konucik | 21/87 |
| 2,462,475 | 2/1949 | DiFilippo | 21/87 |
| 3,419,346 | 12/1968 | Nicholas | 21/87 |
| 3,454,352 | 7/1969 | Lamboy et al. | 21/103 X |
| 3,454,353 | 7/1969 | Bjork | 21/103 X |
| 3,488,142 | 1/1970 | Cooper | 21/103 X |
| 3,511,593 | 5/1970 | Thomas et al. | 21/103 X |
| 3,579,290 | 5/1971 | Pickstone | 21/99 X |
| 3,966,408 | 6/1976 | Drennen et al. | 21/87 |

Primary Examiner—Barry S. Richman
Attorney, Agent, or Firm—C. Bruce Hamburg

[57] ABSTRACT

A cold sterilizer comprises a tray for containing a sterilant and instruments to be sterilized, a lid fitting over the tray, a timer for measuring the period for which the instruments are to be contained in the sterilant to effect sterilization and means for resetting the timer to its original setting for a sterilization upon lifting the lid from the tray during the sterilization. The sterilizer may further comprise means for locking the lid onto the tray and means operatively connecting the timer to the locking means so that the locking means is locked while the timer is timing a sterilization and the locking means unlocks when the period for which the timer is set has expired. There may also be provided means for manually overriding the timer and unlocking the locking means during a sterilization and for thereupon resetting the timer to its original setting for the sterilization.

3 Claims, 6 Drawing Figures

COLD STERILIZER

BACKGROUND OF THE INVENTION AND PRIOR ART STATEMENT

This invention relates to a cold sterilizer.

Cold sterilizations are conducted by immersing the articles being sterilized in an unheated chemical sterilant, hence the characterization "cold". Such sterilizations are more convenient than autoclaving or the use of other hot sterilizers and, hence, are frequently used for instruments by doctors and dentists. An inadequate duration of contacting of the instruments with the sterilant can, however, result in incomplete sterilization. In a busy medical or dental office or hospital, the risk of such accidents may be substantial.

Many hot sterilizers have been provided with timers. Exemplary ones are those disclosed in U.S. Pat. Nos. 3,450,489 and 3,879,171. These timing devices depend, however, upon the attentiveness of the operators and, moreover, in some instances, where they are heat-activated, as in U.S. Pat. No. 3,450,489, they are not suitable for cold sterilizers.

It is, therefore, an object of the invention to provide a cold sterilizer having automatic means to help assure that objects being sterilized are not prematurely withdrawn from the sterilant.

Other objects and advantages of the invention will be apparent from the following description of the invention.

SUMMARY OF THE INVENTION

According to the invention, there is provided a cold sterilizer comprising a tray for containing sterilant and instruments to be sterilized, a lid fitting over the tray, a timer for measuring the period for which the instruments are to be contained in the sterilant to effect sterilization and means for resetting the timer to its original setting for a sterilization upon lifting the lid from the tray during the sterilization. The sterilizer may further comprise means for locking the lid onto the tray and means operatively connecting the timer to the locking means so that the locking means is locked while the timer is timing a sterilization and the locking means unlocks when the period for which the timer is set has expired. There may also be provided means for manually overriding the timer and unlocking the locking means during a sterilization and for thereupon resetting the timer to its original setting for the sterilization.

These and other features of the invention will be described with greater particularity by reference to a specific embodiment of the invention as illustrated in the drawings.

DESCRIPTION OF PREFERRED EMBODIMENTS

Figure 1:
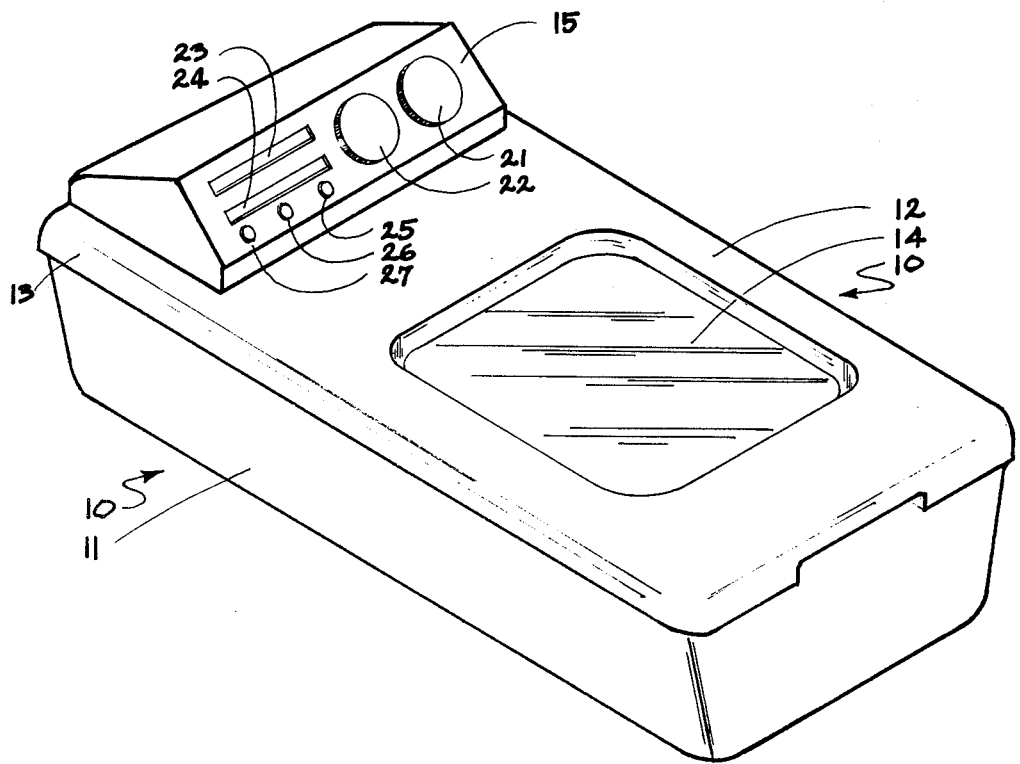
FIG. 1 is an isometric view of a cold sterilizer according to the invention.

A cold sterilizer 10 of the invention includes a deep tray 11 for containing the sterilant and the instruments to be sterilized and a lid 12 which is hinged to the tray at 13 (FIG. 1). The lid 12 is provided with a window 14 to permit observation of the contents of the sterilizer 10. Mounted on the lid 12 is a control and display unit 15 for the sterilizer 10.

Figure 2:
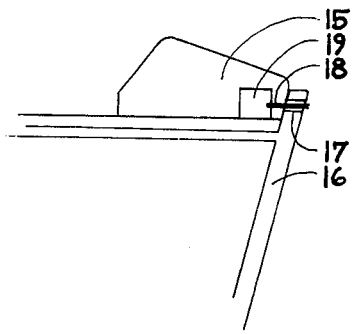
FIG. 2 is a partially sectional side elevation of a detail of the sterilizer of FIG. 1.

For the purpose of locking of the lid 12 onto the tray 11, an end wall 16 of the tray 11, opposite the end of the tray 11 at which the lid 12 is hinged to the tray 11, is provided with an orifice 17 for receiving a locking pin 18 which is attached to the armature of a solenoid 19 (FIG. 2), the solenoid 19 being housed in the control and display unit 15.

Figure 3:
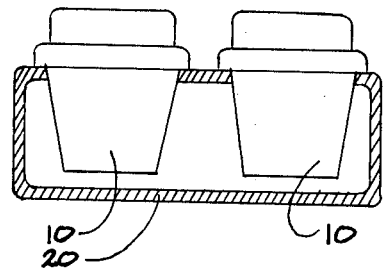
FIG. 3 is a front elevation of a pair of the sterilizers of FIG. 1 in a ganging frame.

Two or three or four or so forth of the sterilizers 10 may be supported in a ganging frame 20 (FIG. 3) which may be placed on a counter top or supported in an opening provided in a counter top for that purpose, the latter essentially in the same manner as a sink is supported in an opening in a counter top.

The control and display unit 15 includes two timers 21 and 22, two digital displays 23 and 24, one for each of the timers 21 and 22, and three signal lights 25, 26 and 27 (FIG. 1). When the light 25 is on, that means the sterilizing cycle is over. When the light 26 is on, that means the sterilizing cycle is in progress. When the light 27 flashes, that means the sterilizing cycle has been interrupted. These light signals may be replaced by or augmented with audible signals. The timer 21 is a relatively short duration timer, for example, one hour, which is manually set after the instruments have been immersed in the sterilant in the tray 11 and the tray 12 has been closed. Setting of the timer 21 actuates the solenoid 19 to lock the lid 12 onto the tray 11. Simultaneously, the setting of the timer 21 actuates the digital display 23 to display the time interval for which the timer 21 has been set. As the time set on the timer 21 elapses, the display 23 counts backwards to zero. When the timer 21 reaches zero, the solenoid 19 is thereby actuated to unlock the lid 12 from the tray 11. The timer 22, which is optional, is a long duration timer. For example, the maximum interval for which the timer 22 may be set may be a week or longer. The setting of the timer 22 actuates the digital display 24 to display the time interval for which the timer 22 has been set. As the time set on the timer 22 elapses, the display 24 counts backwards to zero. When the timer 22 reaches zero, the solenoid 19 is actuated to lock the lid 12 to the tray 11 and the control and display unit is otherwise completely shut down. The timer 21 serves to prevent the removal of instruments from the sterilant before they have been in the sterilant for sufficient time to assure sterilization. The timer 22 prevents the continued use of the sterilant past the effective life thereof. The timers 21 and 22 are for the purpose of preventing unintentional removal of instruments before they have been in the sterilant long enough or unintentional continued use of the sterilant past its effective life. These controls can be overridden. To do so, however, requires a discrete, different mechanical act which one could not do unintentionally. Specifically, locking of the lid 12 to the tray 11 effected by either or both of the timers 21 an 22 is overridden by manually depressing the pin 18 sufficiently to disengage it from the orifice 17. With respect to the timer 22, when one overrides the timer 22 in this manner, the purpose is to permit one to discharge the used sterilant from the tray 11 and pour fresh sterilant into the tray 11. With respect to the timer 21, when one overrides the timer 21 in this manner, the purpose is to permit one to load additional instruments into the tray 11. The manual depressing of the pin 18 automatically resets the timer 21 to its original setting so that all the instruments will remain in the sterilant for at least the period of time for which the timer 21 was originally set without one having to remember which instruments were added later. This will repeat regardless of how many times the cycle is interrupted.

Figure 4:
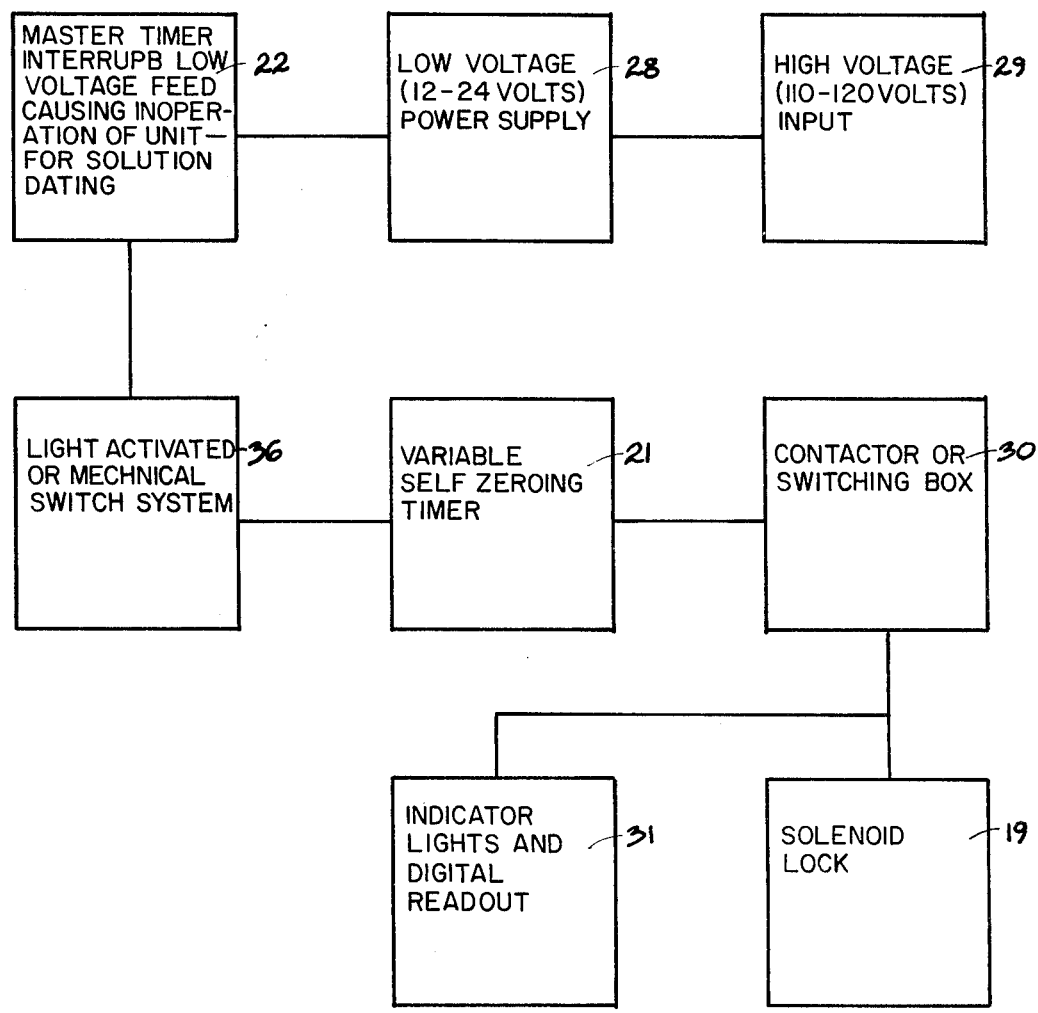
FIG. 4 is a block diagram of the power and control system of the sterilizer of FIG. 1.

The block diagram (FIG. 4) schematically illustrates the workings of the control and display unit 15. Circuit diagrams have not been presented since each of the items represented by a block is of conventional manufacture and readily commercially available. The unit 15 includes a low voltage (12–24 V.) power supply 28 which is plugged into a high voltage input 29 (for example, normal residential current of 110–220 V.). The low voltage power supply 28 is connected to a light activated or mechanical switch system 36 through the timer 22. The system 36 is connected to the timer 21 and the timer 21 is connected to a contactor or switching box 30 to which are connected in parallel a unit 31, constituted of the indicator lights 25, 26 and 27 and the digital displays 23 and 24 and the solenoid 19.

Figure 5:
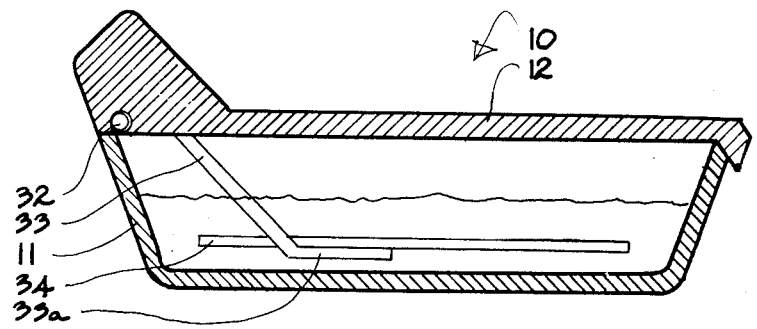
FIG. 5 is a partly sectional side elevation of a sterilizer of the invention with the lid up.
Figure 6:
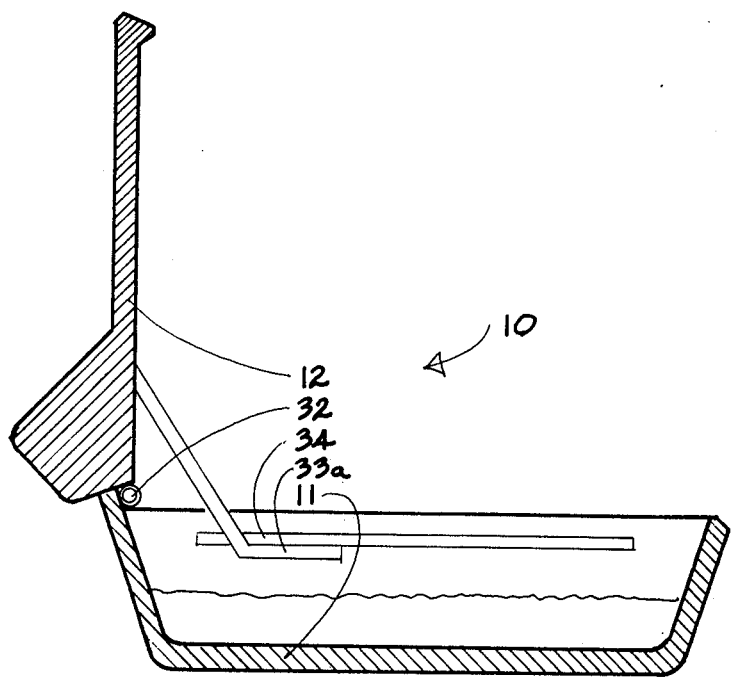
FIG. 6 is a view like FIG. 5 but with the lid down.

FIGS. 5 and 6 illustrate another feature of the sterilizer of the invention which is optional, namely, a rack for the instruments being sterilized, which rack lifts from the sterilizing liquid when the sterilizer lid is opened. The lid 12 is hinged to the tray 11 by hinge means 32. Rack support means 33 is pivotally connected by conventional means (not illustrated) to the lid 12 so that it can pivot between the orientation relative to the lid 12 illustrated in FIG. 5 and that illustrated in FIG. 6. Associated with the rack support means 33 is a horizontal rack 34. The horizontal rack 34 is arranged in the tray 11 so that it is free to move vertically but cannot shift horizontally. This can readily be accomplished by any one of many mechanical arrangements, such as by providing projections on the rack 34 to be guided in vertical racks provided in the walls of the tray 11, just by way of example. The rack 34 is not rigidly connected to the rack support means 33 but is supported by the horizontal portion 33a of the rack support means 33 so that the horizontal portion 33a is horizontally slidable relative to the rack 34 in the front-to-back and back-to-front directions of the tray 11. From the foregoing, it is, of course, apparent that the rack will be lifted from the position illustrated in FIG. 5 to the position illustrated in FIG. 6 when the lid 12 is opened and vice versa when the lid 12 is closed.

It is intended that the invention as defined by the hereto appended claims also include modifications and variations of the foregoing. For example, the sterilizer may be provided with an ultrasonic transducer to facilitate gross cleaning and sterilization.

What is claimed is:

1. A cold sterilizer comprising a tray for containing sterilant and instruments to be sterilized, a lid fitting over the tray, a sterilization timer for measuring the period for which the instruments are to be contained in the sterilant to effect sterilization, means for resetting the timer to its original setting for a sterilization upon lifting the lid from the tray during the sterilization, means for locking the lid onto the tray and means operatively connecting the timer to the locking means so that the locking means is locked while the timer is timing a sterilization and the locking means unlocks when the period for which the timer is set has expired and means for manually overriding the timer and unlocking the locking means during a sterilization and for thereupon resetting the timer to its original setting for the sterilization.

2. A sterilizer according to claim 1, including first and second timers, said first timer being said sterilization timer, said second timer being a longer duration timer than said first timer for measuring the period for which the sterilant is to remain in the sterilizer before discharging the sterilant on the basis that the effective life thereof is expired, and means operatively connecting the second timer to said locking means so that the second timer actuates locking of said locking means when the period for which the second timer is set has expired.

3. A sterilizer according to claim 2, comprising a power supply, said second timer being electrically connected in series to said power supply, first switch means electrically serially connected to said second timer, said first timer being electrically serially connected to said first switch means, second switch means electrically serially connected to said second timer, indicator means for indicating the operating mode of the sterilizer, said locking means and said indicator means being electrically connected in parallel to said second switching means.

* * * * *